United States Patent [19]
Malluche et al.

[11] Patent Number: 4,839,194
[45] Date of Patent: Jun. 13, 1989

[54] METHODS OF PREPARING TISSUE SAMPLES

[75] Inventors: Hartmut H. Malluche; Gisela Malluche, both of Lexington, Ky.

[73] Assignee: Bone Diagnostic Center, Lexington, Ky.

[21] Appl. No.: 751,960

[22] Filed: Jul. 5, 1985

[51] Int. Cl.[4] .......................... A01N 1/00; G01N 1/28; G01N 1/30

[52] U.S. Cl. ........................................... 427/2; 424/3; 427/4; 427/45.1; 427/443; 436/164; 436/174

[58] Field of Search ..................... 435/3; 436/174, 164; 427/45.1, 4, 2, 54.1, 322, 443; 424/3; 264/109, 239

[56] References Cited

U.S. PATENT DOCUMENTS

| | | | |
|---|---|---|---|
| 3,679,450 | 7/1972 | Berghtol | 427/2 |
| 3,961,097 | 6/1976 | Gravlee, Jr. | 427/2 |
| 4,205,059 | 5/1980 | von Hagens | 427/4 |
| 4,545,831 | 10/1985 | Ornstein | 156/57 |
| 4,656,047 | 4/1987 | Kok et al. | 427/4 X |

FOREIGN PATENT DOCUMENTS

| | | | |
|---|---|---|---|
| 0043127 | 11/1974 | Japan | 427/45.1 |
| 0219005 | 12/1983 | Japan | 427/45.1 |

OTHER PUBLICATIONS

Login et al., Am. J. Pathol., vol. 120, pp. 230–243, 1985.

Brinn, J. of Histotechnology, vol. 6, No. 3, pp. 125–129, 9/1983.

Login, Am. J. Med. Technol., vol. 44, pp. 435–437, 1978.

Boon et al., Histopathology, vol. 10, pp. 303–309, 1986.

Hopwood et al., Histochemical Journal, vol. 16, pp. 1171–1191, 1984.

Leong et al., J. of Pathology, vol. 146, pp. 313–321, 1985.

Chew et al., Cell Biology International Reports, vol. 7, No. 2, pp. 135–139, 2/1983.

Gordon et al., Am. J. Med. Technol., vol. 40, No. 10, pp. 441–442, 10/1974.

Patterson et al., Stain Technology, vol. 55, No. 2, pp. 71–75, 1980.

Petrere et al., *Stain Technology,* vol. 52, No. 2, pp. 113–114, 1977.

Hopwood et al., Biosis Previews, 69–86, Biosis No. 79050815 (1984).

*Primary Examiner*—Robert J. Hill, Jr.
*Attorney, Agent, or Firm*—A. W. Breiner

[57] ABSTRACT

A method is described for preparing tissue samples for use in diagnostic evaluation involving the rapid fixation, dehydration, and embedding of a tissue sample as well as rapid mounting of plastic sections to glass slides, dissolution of plastic and optimal staining of tissure components. The rapid and controllable fixation and the dehydration of the tissue sample utilizes the denaturing effects of microwaves on the proteins in combination with a heat sink. Alternatively, the dehydration of the tissue sample utilizes the principles of freeze drying. The tissue sample can be embedded using conventional paraffin embedding or plastic embedding techniques. Rapid penetration of plastic into the tissue is facilitated by microwaves, adhesion of plastic sections to glass slides is promoted by microwaves, as is the fast and optimal staining of tissue components. The method of this invention provides a very rapid technique for processing of tissue for diagnostic and analytic evaluation.

15 Claims, No Drawings

METHODS OF PREPARING TISSUE SAMPLES

FIELD OF THE INVENTION

The invention relates to a method of preparing tissue samples which are to be used in diagnostic evaluation, such as microscopic examination. The preparation of tissue samples in accordance with this invention involves the rapid fixation, dehydration, and embedding of a tissue sample and subsequent adhesion of plastic sections cut from a tissue sample to glass slides and staining of these slides. The rapid fixation of the tissue sample involves exposure of the tissue sample to microwaves in the presence of a heat sink. Dehydration of the tissue sample involves the principle of repeated exposure to microwaves in the presence of the heat sink or the principle of freeze-drying for larger tissue samples, in particular bone samples. The tissue sample may be embedded using a conventional paraffin or plastic embedding technique. Rapid penetration of the plastic into the tissue is accomplished by using microwaves. Rapid adhesion of the plastic sections to glass slides is facilitated by using microwaves as is the rapid and optimal penetration of histologic stains into the various tissue components.

BACKGROUND OF THE INVENTION

It is known in the art to prepare a tissue sample which is to be used for diagnostic evaluation by first fixating the tissue sample followed by dehydration and embedding of the tissue sample. The conventional methods for fixation and dehydration of tissue specimens, however, are time consuming and utilize potentially toxic substances which release or may release malodorous vapors.

One conventional fixation technique uses formalin or formalin derivatives. Formalin is an aqueous solution of formaldehyde which may contain methyl alcohol. This conventional fixation method requires 8 to 24 hours for completion of the fixation process.

Conventional dehydration techniques use ethanol, toluene, or other organic solvents which are flammable, volatile, and potentially toxic. Time requirements for the conventional dehydration techniques are between 8 hours and four days.

In the past, improvements to fixation techniques have been attempted by using heat in order to accelerate the fixation of a tissue specimen. However, past fixation techniques using heat have been detrimental to the tissue specimen due to overheating or burning of the tissue specimen resulting in the loss of the tissue sample.

Conventional embedding techniques use paraffin or plastic monomers which undergo polymerization induced by benzoyl peroxide and heat. Sections of tissue samples embedded in paraffin are of inferior quality compared to plastic embedded samples. However, most plastic embedded techniques are time consuming, i.e., between 36 to 58 hours are required for optimal plastic embedding.

Conventional methods for adhesion of plastic sections to glass slides use pressure application combined with moderate heat. This approach requires between 8 to 18 hours.

Conventional techniques for plastic embedding do not remove the plastic from the tissue section. The presence of the plastic in the tissue section affects the affinity of the histologic stains to the cells. Dissolving of plastic is rarely done and, if so, requires in the range of 1.45 hours per set of tissue sections.

Conventional methods for staining of histologic sections use immersion of slides into containers filled with the particular histologic stains. Differential exposures to different stains result in preferential identification of various tissue components by selective staining. Conventional staining techniques such as trichrome stains require up to 80 minutes for completion of selective sequential staining.

OBJECTS OF INVENTION

It is an object of this invention to provide a new rapid fixation technique using the protein denaturing effects of microwaves without any detrimental effect on the tissue specimen due to heat.

Another object of this invention is to provide a new rapid fixation technique which results in the fixation of various tissues within 10 seconds to 20 minutes.

Another object of this invention is to provide a rapid dehydration technique which when used in conjunction with the rapid fixation techniques of this invention provides dehydration of a tissue sample within 1 to 3 hours.

Another object of this invention is to provide a rapid dehydration technique which utilizes the protein denaturing effects of microwaves without any detrimental effect on the tissue specimen due to heat.

Another object of this invention is to provide a rapid penetration technique for plastic embedding utilizing non-thermal and thermal effects of microwaves as accelerating principle for penetration of plastic monomer into tissue specimens.

Another object of this invention is to provide for the rapid penetration of plastic into various tissues within 15 to 315 minutes.

Another object of this invention is to provide a new approach for faster adhesion of plastic sections to glass slides utilizing the thermal effects of microwaves requiring approximately 10 minutes.

Another object of this invention is to provide a new technique for the removal of the plastic polymer from tissue sections utilizing the thermal effects of microwaves requiring approximately 6 minutes.

Another object of this invention is to provide a rapid technique for differential staining of tissue components utilizing thermal and non-thermal effects of microwaves.

It is a further object of the present invention to provide an overall process of preparing tissue samples involving fixation, dehydration, embedding of the tissue sample, rapid adhesion of sections to slides, and optimal staining technique for use in diagnostic evaluation which involves a reduction in time as compared to conventional tissue preparation methods and utilizes substances of no or limited toxicity and produces no or minimal toxic fumes or odors.

The aforesaid objects, and other objects, of the present invention will be apparent from the following brief description of the invention and detailed description of the preferred embodiments.

BRIEF DESCRIPTION OF INVENTION

The method of preparing a tissue sample in accordance with this invention for use in diagnostic evaluation, such as in microscopic examination, involves the rapid fixation, dehydration, embedment, adhesion to plastic slides, plastic removal and the rapid staining of tissue components. The rapid fixation process involves the exposure of a tissue specimen to a source of microwaves. A heat sink is present in conjunction with the tissue specimen thereby allowing the non-thermal effects of the microwaves to prevail and fixate the tissue specimen. Thereafter, the tissue sample is dehydrated by immersing the tissue specimen in an alcoholic solution associated with repeated exposure to microwaves with a heat sink or by the freeze-drying of the tissue specimen to be dehydrated. Subsequent to the fixation and dehydration steps, the tissue sample is embedded using conventional paraffin embedding techniques or a rapid plastic embedding technique with utilization of microwaves for fast penetration of the plastic, dissolution of the plastic after cutting, and adhesion of tissue sections to gelatin coated glass slides. Thereafter, tissue sections are stained utilizing microwaves for fast and optimal selective differential staining of the various tissue components.

As will be apparent, the fixation, dehydration, penetration as part of the embedding, adhesion to glass slides, removal of plastic and staining techniques can be used individually or in a combination process. Also, as will be apparent, the techniques of this invention can be used on all types of tissues including muscle, bone, skin, liver, kidney, brain, endocrine organs, samples of GI tract, gynecological specimens, lungs, otolaryngeal specimens, etc.

DETAILED DESCRIPTION AND PRESENTLY PREFERRED

EMBODIMENT OF INVENTION

Although the method of preparing tissue samples for use in diagnostic evaluation, as described in this invention, is suitable for use with all types of tissue, including muscle, bone, skin, liver, kidney, brain, endocrine organs, sample of the GI tract, gynecological specimens, lungs, otolaryngeal specimens, etc., the method of tissue sample preparation is especially useful in the preparation of undecalcified bone samples. Previously, mineralized bone histology has been tedious, complicated and time-consuming and, therefore, performed only in a few select laboratories. The present invention allows for the preparation of mineralized bone samples to be included in routine diagnostic tests. The time requirements under the present invention of the preparation of a section of a mineralized bone sample is 16 to 20 hours as compared to 1 to 4 weeks needed by the conventional techniques presently used in mineralized histology.

The first step in the preparation of a tissue sample useful in diagnostic evaluation is the fixation of the tissue sample. The denaturing effect of microwaves on proteins is used to achieve a rapid and controllable fixation of the tissue sample. A heat sink is used in conjunction with the microwave emission source or microwave radiation so that only the non-thermal effects of the microwaves will prevail upon the tissue sample thereby avoiding any detrimental effect overheating could have on the tissue sample.

Specifically, the preferred method of fixation of the present invention involves the placement of the tissue specimen in the container sufficient in size to hold a large volume, i.e., approximately 4 liters, of a solution suitable as a liquid fixation medium such as ethanol, physiologic saline, or 10% buffered formalin. Alternatively, the tissue specimen can be placed repeatedly in smaller containers, such as staining dishes, filled with a smaller volume of one of the liquid fixation mediums as above described, or the tissue specimen can be carried, once in a staining dish, with a solution, such as 100% ethanol, at a temperature of less than 0° C. (up to −40° C.). The tissue specimen(s) in the container is(are) then exposed to a microwave emission source. The length of exposure time of the tissue sample(s) to microwaves during the fixation process depends on the size and consistency of the tissue sample(s). The principle of the heat sink avoids buildup of temperature in the tissue and its surrounding solution by (a) use of large volumes of solution; or (b) repeated exposure to microwaves with transferrals of the sample to new containers filled with small solutions at temperatures between 2° C. and 10° C., or (c) one-time exposure of the sample to microwaves while the sample is placed in a solution at temperatures of less than 0° C. (up to −40° C.). In either event, the temperature of the solution or liquid carrier will preferably be below 10° C. The principle of the heat sink implies a direct relationship between volume of solutions and lowering of temperatures, i.e., the smaller the volume of solution in which the sample is placed the lower the temperatures must be to avoid build-up of heat. For example, in the case of a bone sample, the average bone sample obtained for diagnostic evaluation is 0.5×2.5 cm. A bone sample of such size is fixated within 90 seconds after exposure to microwaves when placed in a container filled with 400–500 ml 100% ethanol at a temperature of −40° C. or within 10 minutes when placed in a container filled with 4 liters of 100% ethanol at a temperature of −10° C. Other solutions such as physiologic saline and buffered formalin require more microwave exposure to be heated and, therefore, fixation of bone samples of the above size is possible within 10 minutes when the sample is placed in 4 liters of these solutions at 2° C. (solutions stored in the refrigerator) or exposed to microwaves in a container filled with 4 liters of these solutions. The temperature in the immediate vicinity of the bone sample preferably should not exceed 38° C. The working ranges of the temperatures after completion of fixation usually are between 10° C. and 40° C. The preferred solution for immersion of the tissue during the fixation process is ethanol for bone and liver, formalin for kidney, and saline for brain. When soft tissue samples are fixated, starting temperatures below −5° C. are avoided because of possible damages of the more peripheral cells of the sample. It is preferable to choose sequential exposure to microwaves when larger soft tissue samples are to be fixated such as two exposures for 7 minutes each, i.e., 2×7, in 4 liters at −5° C. Any microwave emission source may be utilized which complies with operation and safety standards set for kitchen microwave ovens. The microwave power should be set between 500–600 Watt, and the samples should be centered and placed freely suspended in the container to ensure optimal exposure.

Following the fixation of the tissue sample, the sample is rapidly dehydrated using microwaves or the principles of freeze-drying. When using microwaves, the sample should be placed freely suspended in the center of a solution-filled container to ensure optimal exposure of all surfaces to the microwaves. The preferred solution is 100% ethanol; however, any similar alcoholic solution is suitable. Application of the principle of the heat sink is again necessary and is optimally done if the sample is repeatedly placed in 1800 ml of ethanol and repeatedly exposed to microwaves. It is of note that the ethanol should be renewed after each exposure to microwaves when a given number of tissue samples are dehydrated in it. Working range of exposure is between 4 to 6 times 20 minutes at 24–36 Watt starting at room temperature. Application of microwaves with a heat sink is useful for soft tissue and smaller sized bone samples. Larger bone samples, in particular samples with a large fraction of the surface consisting of compact bone, are preferably dehydrated using freeze-drying principles. Specifically, a tissue sample is preferably dehydrated by immersing the specimen in about 300 ml of 100% ethanol at $-5°$ C. to $-10°$ C. in a lyophilizer flask having a volume of 600 ml. The tissue sample is then freezedried for 1-1.5 hours, depending on actual sample size and fraction of outer surface consisting of compact bone. Repeated application after exchange of the ethanol may be needed in extreme cases. It is possible to dehydrate human bone samples without the use of an anhydrous liquid. This procedure is less safe since it is critical to meet the optimal time for dehydration. Under-exposure results in an unacceptable section quality, and over-exposure produces multiple artifacts. A freeze dryer such as the Labconco freeze dryer Model 8 equipped with a Directorr vacuum pump may be used for freeze-drying the tissue samples. The chamber pressure of the freeze dryer is between 1000 and 400 torr having a starting temperature of $-50°$ C.

Following the fixation and dehydration of the tissue sample, the tissue sample is embedded using a conventional paraffin embedding technique or a plastic embedding technique.

The present invention includes utilization of microwaves for rapid plastic embedding. The use of microwaves provides for the rapid penetration of the plastic monomer into the various soft tissues or bone. Before a sample is placed in the liquid plastic monomer, a transition step is needed. The tissue sample is placed in a suitable container, such as a staining dish, filled with 500 ml of a 1:1 mixture of ethanol and pure methyl methacrylate monomer. This container is placed on a magnetic stirrer and stirring action is maintained for 30–45 minutes. Thereafter, the tissue sample can be transferred to another container filled with 450–500 ml of pure methyl methacrylate and exposed to microwaves (24 Watt) for 5 minutes. This exposure to microwaves is repeated twice whereafter the sample is then transferred to a new solution of methyl methacrylate of the same volume starting each time at room temperature. This exposure to microwaves for a total of 15 minutes accomplishes optimal penetration of the plastic monomer into tissue specimens of normal size for diagnostic purposes. Larger specimen, in particular larger bone specimens, require repeated exposure to microwaves or subsequent storage in polymerization solution for 2–8 hours in the refrigerator. Thereafter, the hardening process of the plastic can be started by transferring the tissue sample into a suitable glass jar containing approximately 625 ml of polymerization solution. The polymerization solution consists of 500 ml methyl methacrylate, 125 ml Plastoid N, and 15 gm anhydrous benzoyl peroxide or a multiple or a fraction of these components depending on total volume of plastic needed for embedding. Plastoid N is a mixture of nonylphenol, polyethylene glycol, and ethylacetate.

Polymerization of the plastic with addition of Plastoid N is particularly advantageous in the preparation of undecalcified bone samples since the plastic in which the tissue sample is embedded is hardening to the same or nearly the same hardness as the bone sample embedded in it. Polymerization of the monomer is induced by the addition of benzoyl peroxide initiator, with the final hardness being adjusted by the use of the polyethylene glycol and nonylphenol, both being components of the Plastoid N.

To facilitate optimal penetration of the polymerization solution into bone samples, the samples are kept in the refrigerator for 2–8 hours. This step is not required for soft tissue samples. Thereafter, samples are transferred into glass vials filled with 10–12 ml of the polymerization solution. The glass vials containing the tissue specimens are kept in a warm-water bath at 48°–50° C. until the hardening process is complete (4–8 hours). After hardening of the methyl methacrylate, the glass vials are broken and removed. Other containers such as metal cups may be used and re-used. At this point the tissue sample is permanently embedded in a plastic material which allows the tissue sample to be cut so that it may be used for diagnostic evaluation purposes. A heavy-duty microtome such as the Jung microtome equipped with a D profile knife is used to cut the tissue sample embedded in the plastic. For cutting of soft tissue embedded in plastic or for small bone samples; glass knives and less expensive microtomes are also useful.

Cutting of plastic embedded tissue, especially undecalcified bone, requires specially prepared glass slides for optimal wrinkle-free adhesion of the tissue sections to the slides. The invention also utilizes the thermal effects of microwaves for rapid adhesion of plastic sections to gelatin coated slides. The tissue sections are transferred to the slides, unrolled, and covered with polyethylene plastic paper which is fastened to the slide by a strip of scotch tape. The slide is then transferred into the microwave and exposed for a total of 3 minutes to microwaves emitted at a power of 480 Watt. Thereafter, 10 minutes are allowed for cooling of the slides. The scotch tape is peeled off along with the polyethylene plastic paper, and the tissue section is then attached to the glass slide allowing subsequent staining. An alternate method for adhesion of a plastic section to gelatin coated glass slides may be chosen if time is not of the essence and if bone sections of larger specimen are embedded in plastic and sectioned. This procedure also utilizes polyethylene plastic paper spread over the section which has been stretched with 1–2 drops of stretching fluid (butoxyethanol or 70% ethanol). Again a strip of scotch tape is used to hold the plastic paper onto the glass slide. IT is of note that the polyethylene paper should be carefully stretched over the glass slide, and it should be ascertained that no air bubbles are between the tissue sample and the polyethylene paper or the glass slide and the polyethylene paper. Thereafter, the slides are transferred into an incubator set at 60° C., wherein they remain for a minimum of 30 minutes. A small vice or metal clamp is used to compress a stack of 2–6 glass slides which results in optimal stretching of the tissue sample and adhesion of the plastic section to the glass slides.

After removal of the polyethylene paper, the plastic is removed to allow optimal staining of the various tissue components. Tranferral of slides with plastic sections affixed to them into organic solvents such as 2-methoxy-ethyl-acetate or methyl glycol acetate can be used for dissolution of methyl-methacrylate. Heretofore dipping of glass slides with plastic sections affixed to them into these solutions for a total of 45–60 minutes was required for dissolution of the plastic. This time can be dramatically reduced by the utilization of the thermal effects of microwaves. Approximately ten or so slides can be transferred into a staining jar filled with 65 ml of 2-methoxy-ethyl-acetate. The staining jar is placed into the microwave chamber and exposed for 15 seconds to microwaves emitted at 600 Watt. This procedure is repeated twice, with the slides being transferred each time into a jar filled with a fresh solution of 2-methoxy-ethyl-acetate. Thereafter the slides are transferred into another dish filled with the same solution and allowed to cool down for a total of 2-5 minutes. To clean the slides from the methoxy-ethyl-acetate, the slides are thereafter transferred into three dishes filled with 100% ethanol for 3-5 minutes each time. It is apparent that the total time for the described procedure of plastic removal does not exceed 21 minutes, which represents a further time-saving compared to the previously employed technique.

Thereafter, sections of the various tissues, including bone, need to be stained for proper identification of the various tissue components. Principles of histological staining utilize the affinity of various tissue components to certain stains. The customarily employed staining techniques expose histologic stains for various periods of time. Again, employment of microwaves and their rapid thermal effects are used for fast staining and enhancement of the affinity of certain tissue components to stains used for their identification. The slides are dipped into the staining dishes and thereafter transferred into the microwave oven which is set at 600 Watt. The time requirements for dipping of slides into stains without versus with application of microwaves is listed for the most frequently used bone stains:

Weigert nuclear stain: 10 minutes versus 10 seconds
Ponceau-red: 20 minutes versus 20 seconds
Aniline blue: 2 minutes versus 6-8 seconds
Solochrome-cyanin: 45 minutes versus 45 seconds The tissue samples prepared by the method of the present invention are of superior quality or at least of comparable quality to those prepared by other available methods. The present invention, however, dramatically reduces the turnaround time for processing of tissue samples.

As apparent from the discussion above, variations in the fixation, dehydration, penetration, plastic embedment and dissolution, adhesion to glass slides, and staining techniques in the areas of amount, time, temperature, and material are utilized depending on the size and consistency of the particular tissue specimen. For example, the length of time a tissue specimen may be exposed to microwaves for fixation in the presence of a heat sink can range from 10 seconds to 20 minutes. The total process time necessary for carrying out dehydration of a fixated tissue specimen may take from about 0.25 to 3 hours. The temperature of the liquid carrier in the fixation process may range from −40° C. to room temperature. Additionally, the temperature range of the anhydrous liquid utilized in the dehydration of the tissue sample may range from −40° C. to room temperature. The volume amounts of liquid carriers utilized in the fixation and dehydration steps are also subject to variation. The criteria used in determining the necessary volume of liquid material used in the fixation and dehydration process are determined by the goal to avoid buildup of heat which will inevitably damage the tissues. As outlined above, a higher starting temperature, increasing duration of exposure to microwaves and higher microwave energy will require greater volumes of liquid material to avoid build-up of heat in excess of 40° C. As already stated above, any conventional plastic or paraffin technique may be utilized following the fixation and dehydration stages. Set forth below is an example illustrating a detailed embodiment of the present invention.

EXAMPLE

Preparation of Undecalcified Bone Sections

I. Fixation.

A bone sample having a tissue size of approximately 0.5 cm×3.0 cm is placed in a container filled with 4000 ml of 100% ethanol at a temperature of −10° C. The bone sample should be free-hanging within the fluid, i.e., it should be immersed as deep as possible under the surface, but not closer than 1 cm to the bottom. The container is then placed into a microwave oven with a power set at 600 Watt. The microwave emission source is then activated for a total duration of 10 minutes. At the end of the microwave exposure, the bone sample has been fixated without any burning or other deleterious effects to the sample. The process is repeated if the bone sample exceeds the size mentioned above.

II. Dehydration.

The fixated bone sample is then placed in a container with 1800 ml 100% ethanol at room temperature (20° C.). The microwave emission source is set at 24 Watt and activated for 20 minutes. Thereafter the bone sample is tranferred into another container filled with the same volume (1800 ml) of 100% ethanol at the same starting temperature (20° C.). This procedure is sequentially carried out a total of six times, for 20 minutes each. The total exposure time is 6×20 minutes, or 2 hours. The volume of 1800 ml 100% ethanol can be used for a total of 25 bone samples of standard size. Since the dehydration procedure is sequential, the solutions can be used more than once. The number of the solution corresponds to the step in the sequence. Thus, solution #6 will become solution #5, solution #5 will become #4, solution #4 will become #3, solution #3 will become #2, solution #2 will become #1, and the container #6 will be filled with fresh 100% ethanol. It is again of importance that the samples are free-hanging within the containers; that is, the samples should be fully immersed well below the surface but they should not be closer than 1 cm to the bottom of the container.

For large bone specimens, dehydration utilizing freeze-drying principles can be used as an alternative procedure. The fixated bone sample is placed in a 600 ml volume lyophilizer flask containing 300 ml 100% ethanol at a temperature of −5° C. The bone sample is then freeze dried for 1-1.5 hours. The freeze dryer has a starting temperature of −50° C. and a chamber pressure of 1000 to 400 torr.

III. Plastic Embedding.

The fixated and dehydrated bone sample is placed into a container filled with 500 ml of a solution of 100% ethanol and methyl-methacrylate at equal parts and at room temperature. The container is placed on a magnetic stirrer and a continuous stirring action is maintained for 45 minutes. Thereafter, the bone sample is tranferred into another container filled with 500 ml pure methyl-methacrylate monomer at room temperature. This container is transferred into the microwave oven and the microwave emission source is activated at 24 Watt for 5 minutes. Thereafter, this procedure is repeated 2 times whereby the bone sample is tranferred each time into another container filled with 500 ml pure methyl-methacrylate at room temperature. The temperature of the methyl-methacrylate in the immediate vicinity of the bone sample at the end of the 5 minutes of exposure to microwaves does not exceed 36° C. Thereafter, the bone sample is transferred into another container filled with 625 ml of polymerization solution. The polymerization solution consists of 500 ml methyl-methacrylate monomer, 15 gms of anhydrous benzoyl-peroxide, and 125 ml of Plastoid No. The sample is kept in this solution in the refrigerator for a total of 8 hours. During this period of time, optimal penetration of the polymerization solution is taking place. This is particularly necessary if a larger fraction of the bone sample consists of cortical or compact bone. Thereafter, bone samples are placed in small glass vials filled with 10–15 ml of polymerization solution. The glass vials are transferred into a water bath set at 48°–50° C. The polymerization process is being accelerated by the temperature. Bubble formation is being avoided by the water bath. Total duration for completion of polymerization is between 4–8 hours.

At the completion of the hardening process the glass vials are transferred for 5 minutes into a refrigerator. Thereafter, the glass vials are cracked and the plastic block is removed for cutting. The plastic block contains the fixated and dehydrated undecalcified bone sample suitable for use in diagnostic evaluation.

IV. Adhesion to Slides.

After cutting of the section using a Jung heavy-duty microtome equipped with carbide-edged or D-profiled knives (alternatively glass knives and less expensive microtomes for smaller bone samples), the plastic sections are transferred to gelatin coated slides. Application of one or several drops of stretching fluid (70% ethanol or butoxyethanol) helps stretching of the plastic section. Thereafter, a small (4×2.5 cm) sheet of polyethylene paper is layed over the slide containing the plastic section. The polyethylene paper is attached to the glass slide by a strip of scotch tape. Two to six glass slides are stacked and placed into a small metal vice. The clamp of the vice is tightened to the maximum extent possible without causing breakage of the glass slides and so as to still allow escape of small bubbles of air which might have remained between the plastic paper and the glass slides. The stack of slides held by the vice is then placed into an incubator for 30–60 minutes. Thereafter, the slides held by the vice are removed from the incubator and allowed to cool for two minutes. The slides are then taken out of the vice. If remnants of fluid are still recognizable between glass slides and polyethylene covers, the slides are transferred into a microwave oven and exposed to microwaves at 480 Watt for a total duration of 3 minutes. If time is of the essence, microwave drying without prior placement into the incubator may be used. It is of note, however, that a plastic or glass vice is needed in this case instead of a metal vice. The preferred technique for bones is the slow drying in the incubator, whereas soft tissue can be dried with the microwave only.

V. Removal of Plastic.

The polyethylene covered paper is removed from the slide and the plastic is dissolved for optimal staining of the various tissue components. After the removal of plastic, the slides are transferred into a staining jar filled with 2-methoxy-ethyl-acetate. Dissolution of the plastic is accelerated by placing the jar into a microwave oven and exposing the slides to microwaves emitted at 600 Watt for a total of 15 seconds. This procedure is done three times, with the slides transferred each time into a new jar filled with fresh 2-methoxy-ethyl-acetate. Thereafter, the slides are transferred into another staining jar filled with 2-methoxy-ethyl-acetate at room temperature and allowed to cool down in this solution for another two minutes.

VI. Staining.

To prepare the slides containing the tissue samples for staining, the slides are transferred into three staining jars filled with fresh 100% ethanol at room temperature. The slides remain in each jar for 2–3 minutes. Thereafter, the slides are stained. The preferred stain of the many stains available is Masson-Goldner trichrome stain which allows the differentiation of calcified from non-calcified bone and gives excellent cellular detail. Conventional time needed for immersion of slides into the various stains being part of the Masson-Goldner technique is dramatically reduced by the exposure of the staining jars containing staining fluid and slides to microwaves. In the procedure set forth below, exposure times to microwaves emitted at 600 Watt are listed. Further, the staining jars utilized should be filled with the different stains at room temperature.

Weigert's hematoxylin 10 seconds;
Dip in 100% ethanol;
Rinse in distilled water;
Differentiate in 1% HCL water;
Rinse in tap water (4 times)
Transfer slides in tap water at room temperature to microwave oven;
Exposure in microwave for 20 seconds at 600 Watt;
Rinse in distilled water;
Dip in 1% glacial acetic acid;
Transfer to Ponceau-de-xylidine, room temperature;
Expose 20 seconds to microwaves emitted at 600 Watt;
Rinse in distilled water;
Dip in 1% glacial acetic acid;
Differentiate in 5% phospho molybdic acid until Ponceau-red is removed from trabecular bone (2–5 minutes);
Rinse in distilled water;
Dip in 1% glacial acetic acid;
Transfer to microwave oven in aniline blue at room temperature;
Expose 6–8 seconds to microwaves emitted at 600 Watt;
Clear slide of aniline blue in glacial acetic acid, dehydrate in 100% ethanol (3 times for 1 minute each), clear (3 times for 1 minute each in xylene) and mount;
The bone sample is now suitable for use in diagnostic evaluation.

As will be apparent to one skilled in the art, various modifications can be made within the scope of the aforesaid description. Such modifications being within the ability of one skilled in the art form a part of the present invention and are embraced in the appended claims.

It is claimed:

1. A method of fixation of a tissue specimen comprising placing a tissue specimen in a liquid fixation medium at a temperature below about 10° C., said liquid fixation medium being present in an amount sufficient to provide a heat sink to allow the non-thermal effects of microwave radiation to act on said tissue specimen, and exposing said specimen in said fixation medium to microwave radiation for a time sufficient to fix said tissue specimen while controlling the temperature of said medium so as not to exceed about 40° C.

2. The method according to claim 1 wherein said liquid fixation medium is ethanol at a temperature between about 0° C. and −40° C.

3. A method of dehydrating a tissue specimen comprising placing a tissue specimen in an alcoholic solution, said alcoholic solution being present in an amount sufficient to provide a heat sink to allow the non-thermal effects of microwave radiation to act on said tissue specimen, and exposing said specimen in said alcoholic solution to microwave radiation for a time sufficient to fix said tissue specimen while controlling the temperature of said medium so as not to exceed about 40° C.

4. A method of embedding a tissue specimen in plastic comprising (1) placing a tissue specimen in a solution of plastic monomer and alcohol;

(2) thereaffer, placing said tissue specimen in a solution of plastic monomer and exposing said specimen to microwave radiation;

(3) repeating step (2) twice so that the plastic monomer penetrates into said tissue specimen; and (4) hardening said plastic monomer which has penetrated into said tissue specimen.

5. A method of removing plastic from a tissue specimen which is embedded in plastic and adhered to a slide comprising (1) placing a slide having a tissue specimen adhered thereto in a container filled with an organic solvent;

(2) exposing said slide while in said organic solvent to microwave radiation;

(3) repeating steps (1) and (2), each time transferring said slide to a container filled with a fresh organic solvent solution; and (4) transferring said slide to a fresh organic solvent solution and allowing said slide to cool.

6. The method according to claim 5 wherein steps (1) and (2) are repeated twice and said organic solvent is selected from the group consisting of 2-methoxy-ethyl-acetate and methyl glycol acetate.

7. A method of staining a tissue specimen comprising placing a tissue specimen in a container filled with a 100% alcoholic solution at room temperature with said tissue specimen remaining in said container for about 2–3 minutes, removing said tissue specimen from said alcoholic solution, placing said tissue specimen in a stain and exposing said tissue specimen to microwave radiation.

8. A method of preparing a tissue sample for use in diagnostic evaluation comprising -

(1) placing a tissue specimen in a liquid fixation medium at a temperature below about 10° C., said liquid fixation medium being present in an amount sufficient to provide a heat sink to allow the non-thermal effects of microwave radiation to act on said tissue specimen, and exposing said specimen to microwave radiation present in an amount sufficient to provide a heat for a time sufficient to fix said tissue specimen while controlling the temperature of said medium so as not to exceed about 40° C.;

(2) dehydrating said tissue specimen of step (1); and (3) embedding said tissue specimen of step (2) in an embedding material.

9. The method according to claim 8 wherein said liquid fixation medium is ethanol at a temperature between about 0° C. and −40° C.

10. The method according to claim 8 wherein step (2) comprises placing said tissue specimen in an alcoholic solution and exposing said specimen in said solution to microwave radiation.

11. The method according to claim 8 wherein step (2) comprises immersing said tissue specimen in ethanol at −5° C. followed by freeze-drying said tissue specimen for 0.25 to 3 hours.

12. The method according to claim 8 wherein said tissue specimen is embedded in plastic.

13. The method according to claim 8 wherein said tissue specimen is embedded in paraffin.

14. The method according to claim 8 wherein the embedding step comprises (1) placing the tissue specimen in a container filled with a mixture of ethanol and methyl-methacrylate monomer and continuously stirring the mixture for about 30–45 minutes;

(2) transferring said tissue specimen to another container filled with fresh methyl-methacrylate monomer and exposing said tissue specimen to microwave radiation for about 5 minutes;

(3) repeating step (2) twice so that the methyl-methacrylate monomer penetrates into said tissue specimen; and (4) hardening said monomer which has penetrated into said tissue specimen by polymerization.

15. The method according to claim 14 wherein the step of polymerization comprises (1) placing said tissue specimen in a polymerization solution and keeping said tissue specimen in a refrigerator for a period of about 2–8 hours; and (2) transferring said tissue specimen into a container filled with about 10 to 12 ml of polymerization solution, and keeping said container in a warm-water bath at about 48° C. to 50° C. until hardening is complete.

* * * * *